United States Patent [19]

Huszar

[11] 4,432,376

[45] Feb. 21, 1984

[54] METHOD FOR DETERMINING THE EXTENSIBILITY OF SELECTED NON-EXCISED TISSUE OF THE UTERINE CERVIX, EAR OR SKIN

[76] Inventor: Gabor B. Huszar, 16 Chestnut La., Woodbridge, Conn.

[21] Appl. No.: 230,369

[22] Filed: Jan. 30, 1980

[51] Int. Cl.³ .............................................. A61B 5/10
[52] U.S. Cl. .................................. 128/774; 128/778; 73/823; 33/148 R
[58] Field of Search ............. 128/774, 778; 33/148 R, 33/149 N, 148 E; 73/789, 790, 823

[56] References Cited

U.S. PATENT DOCUMENTS

| | | | |
|---|---|---|---|
| 2,924,220 | 2/1960 | Von Micsky | 128/361 |
| 3,008,239 | 11/1961 | Lange | 128/774 |
| 3,416,363 | 12/1968 | Siems | 73/790 |
| 3,768,459 | 10/1973 | Cannon et al. | 128/25 |
| 3,975,950 | 8/1976 | Erdei | 73/790 |
| 4,127,112 | 11/1978 | Sherlock et al. | 128/774 |
| 4,141,345 | 2/1979 | Allen et al. | 128/361 |
| 4,207,902 | 6/1980 | Krementsov | 128/278 |
| 4,233,743 | 11/1980 | Flick | 128/774 |
| 4,297,884 | 11/1981 | Loveque et al. | 73/789 |
| 4,365,638 | 12/1982 | Loveque et al. | 128/774 |

OTHER PUBLICATIONS

Mechanics of Materials, Laurson et al., Wiley and Sons, New York, N.Y., pp. 23, 25, Au. 244.
Summary Progress Report, National Institute of Health, Bethesda, Maryland, Md., Grant Number HD11227-03, "Stretch Changes in the Rabbit Cervix by Prostaglandin" Conrad, J. T. University of Washington, 1978.

Primary Examiner—C. Fred Rosenbaum
Assistant Examiner—J. L. Kruter
Attorney, Agent, or Firm—DeLio and Libert

[57] ABSTRACT

A method for determining the extensibility of selected non-excised tissue of the uterine cervix, ear or skin by:
(a) positioning the tissue between two force transmitting members, applying a varying compressive force to the tissue through the force transmitting members, measuring the force applied and the displacement of the non-excised tissue resulting from said force, and calculating the modulus of extensibility curve of the tissue, or
(b) positioning the tissue between two force transmitting members, applying a constant compressive force to the tissue through the force transmitting members, measuring the displacement of the tissue resulting from the application of the force, and continuously monitoring the changes in the displacement of the tissue over a period of time to determine the changes in the extensibility of the tissue while the constant force is applied.

8 Claims, 17 Drawing Figures

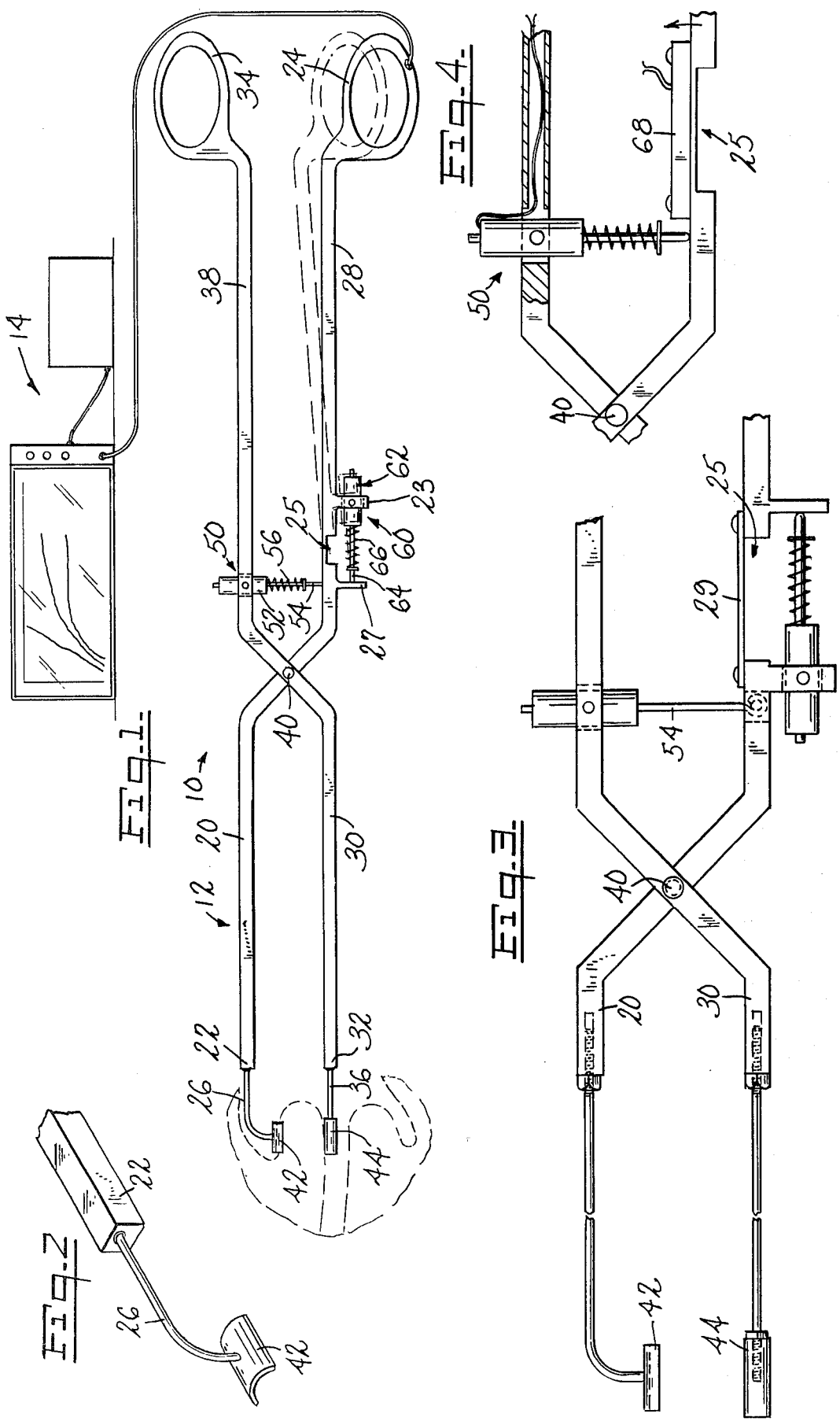

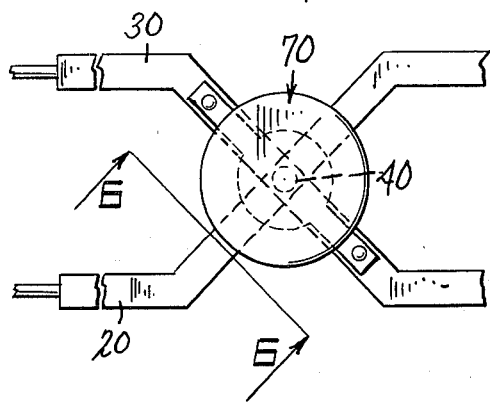
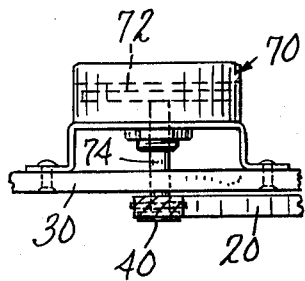
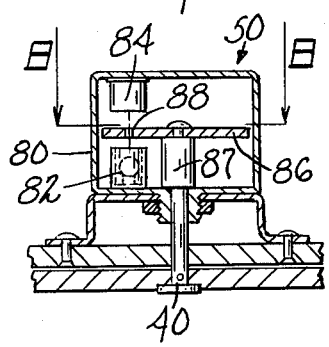
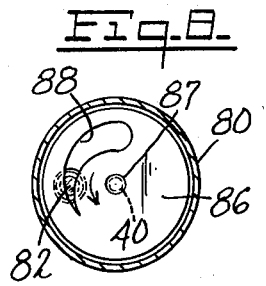
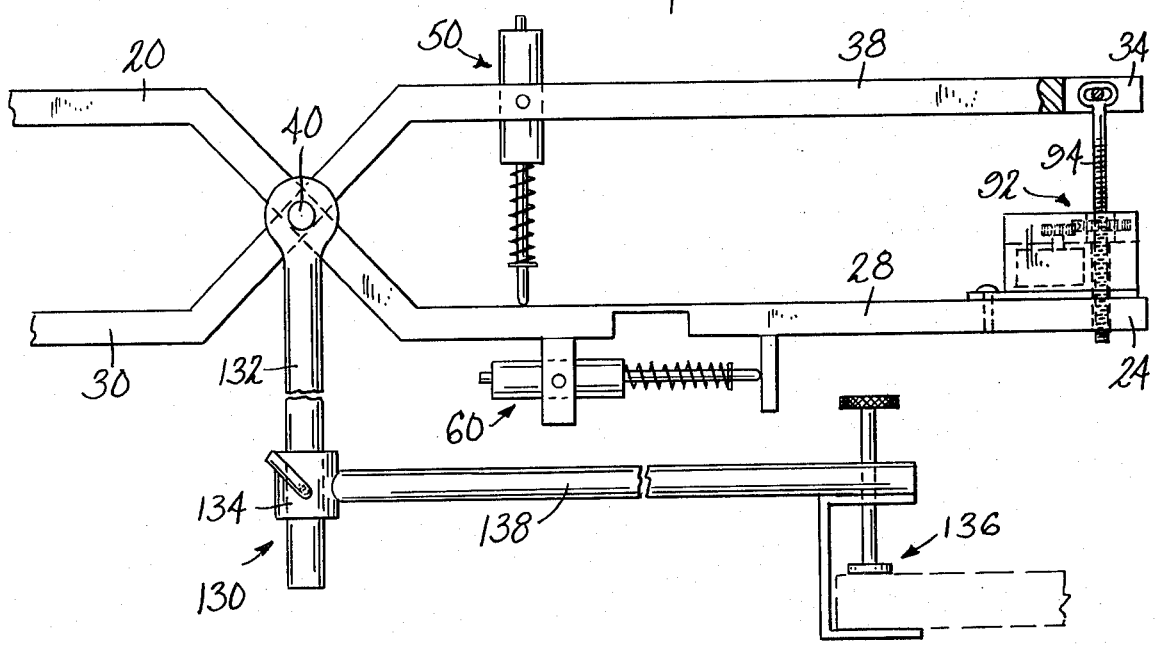

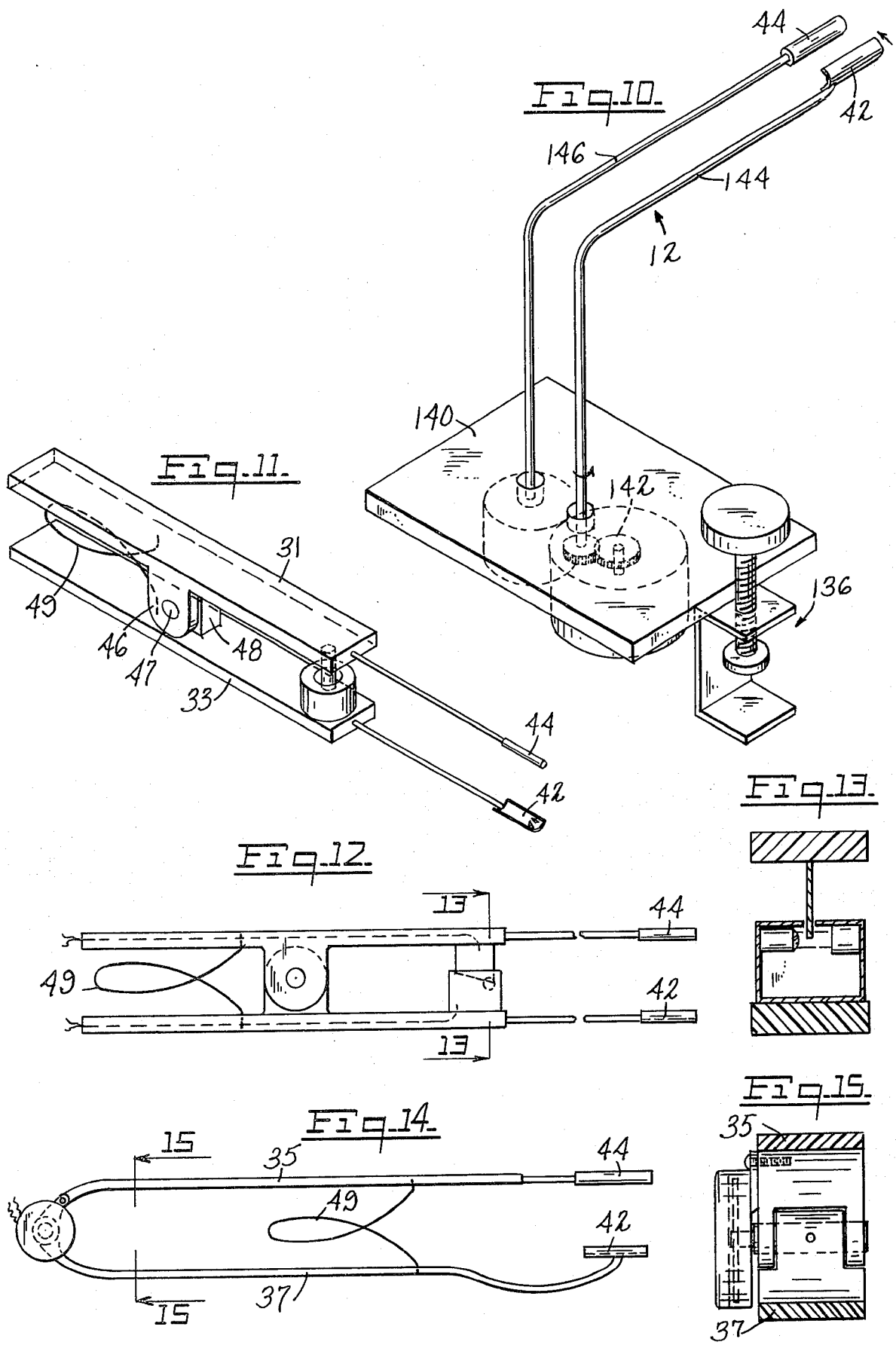

METHOD FOR DETERMINING THE EXTENSIBILITY OF SELECTED NON-EXCISED TISSUE OF THE UTERINE CERVIX, EAR OR SKIN

BACKGROUND OF THE INVENTION

This invention relates to a method and an instrument for measuring the extensibility or pliability of tissue of the uterine cervix. More particularly, this invention relates to a method and an instrument for measuring the condition of the uterine cervix by means of applying a compressive force to the tissue of the cervix and measuring the tissue displacement resulting from the application of the compressive force.

The uterine cervix is both an active participant in the childbirth process and an important indicator of the physical preparation of the mother for childbirth. During the period preceding childbirth, the cervix normally undergoes a maturation process which is closely related to changes in the uterine muscle at the initiation of labor. Throughout labor, the uterine cervix undergoes a transition (including softening, thinning and dilation) some of which can be measured by various methods.

Prior instruments directed to quantifying the physical characteristics of the uterine cervix have been primarily directed to measurement of the dilation of the cervix during labor. Such instruments essentially measure the diameter of the cervical opening. While there can be little doubt that the measurement of dilation is a general indicator of the condition of the uterine cervix during labor, a more fundamental characteristic of the condition of the uterine cervix is the pliability or extensibility of the cervical tissue. This invention is based on the principle that changes in compressibility and extensibility of the cervix are related, as they are results of the underlying biochemical processes in the cervix. Thus, the ratio of the applied force to the tissue displacement represents a quantity indicative of tissue extensibility.

Prior related instruments have not provided for continuous monitoring of the cervix preceding and during labor. The present invention is directed to measuring changes of the uterine cervix throughout the labor process without requiring multiple vaginal examinations by an individual who monitors and supervises the cervical effacement (thinning) process. The present invention is not only capable of continuous monitoring, but it is capable of producing a more comprehensive and analytical picture of the condition of the uterine cervix and transmitting the information to a central monitoring facility (e.g. nursing station in hospital).

It is noted that the present invention may be employed in connection with a wide range of obstetrical and gynecological conditions such as premature labor, infertility, endocrine disorders and tumors. The invention is also applicable for use in connection with tissues other than the cervix, such as tissue of the ear or skin, and may be used in many non-obstetrical/gynecological applications.

SUMMARY OF THE INVENTION

The invention comprises an instrument having a pair of arms which are adapted to engage at the interior and exterior of either the anterior or posterior lip of the uterine cervix. A compressive force generated between the arms impinges on the tissue of the lip of the cervix. The instrument measures the compressive force and the resultant displacement of the tissue under the compressive force. The measurements are employed to produce a third measurement (i.e. modulus) which is indicative of the compressibility/extensibility of the tissue.

An alternate embodiment of the invention employs an instrument having arms biased under a constant compressive force. Measurement of the resultant displacement of the tissue at the lip of the cervix forms the data input which is used to indicate the compressibility/extensibility of the tissue of the cervix as well as its thickness during labor.

The invention is also directed to a method for measuring the extensibility of the tissue of the uterine cervix by application of a compressive force on the tissue, measurement of the displacement of tissue resulting from the application of force, and calculation and production of an output responsive to the measurement and applied force.

OBJECTS OF THE INVENTION

An object of this invention is to provide a new and improved method and a new and improved instrument for measuring changes of the uterine cervix in pregnancy, labor and other related obstetrical and gynecological conditions.

Another object of this invention is to provide a new and improved method and a new and improved instrument for measuring the extensibility of the tissue of the uterine cervix and indicating the condition of the uterine cervix relative to characteristics determined from other such measures.

Another object of this invention is to provide a new and improved method and a new and improved instrument for measuring the extensibility of the tissue of the uterine cervix in a manner which is independent of the diameter of the opening of the cervix.

A further object of this invention is to provide a new and improved method and a new and improved instrument which produces a more reliable indication of the condition of the uterine cervix during pregnancy, premature labor, labor and other obstetrical and gynecological conditions.

A still further object of this invention is to provide a new and improved method and a new and improved instrument for continuously measuring and monitoring the compressibility of the tissue of the uterine cervix throughout the labor process.

A still further object of this invention is to provide a new and improved instrument which is easy to operate and can be applied to a continuous automatic monitor or radiotransmitter to dispense with the necessity of multiple vaginal examinations and the continuous physical presence of an operator.

Other objects and advantages will become apparent from the detailed description and the accompanying drawings.

BRIEF DESCRIPTION OF THE DRAWINGS

FIG. 1 is a side view of the cervical measurement instrument, parts of which are illustrated schematically, engagement with the uterine cervix being partially shown in section.

FIG. 2 is an enlarged perspective view of a portion of the instrument shown in FIG. 1.

FIG. 3 is a side view of a portion of an alternate form of the cervical instrument shown in FIG. 1.

FIG. 4 is a side view of a portion of another embodiment of the cervical instrument, partly in section.

FIG. 5 is an enlarged side view of the central portion of one embodiment of the cervical instrument.

FIG. 6 is a sectional view taken along line 6—6 of FIG. 5.

FIG. 7 is a side sectional view of an alternate form of the portion shown in FIG. 5.

FIG. 8 is a sectional view taken along line 8—8 of FIG. 7.

FIG. 9 is a side view of an alternate embodiment of the cervical instrument, parts being broken away and part of the instrument being illustrated schematically.

FIG. 10 is a perspective view of a portion of still another form of the cervical instrument, parts of the drawing being broken away to illustrate details.

FIG. 11 is a perspective view of a portion of a cervical instrument which can be employed for continuous monitoring.

FIG. 12 is a side view of an alternate embodiment of the instrument portion shown in FIG. 11.

FIG. 13 is a sectional view of the instrument of FIG. 12 along the line 13—13.

FIG. 14 is a side view of a portion of another form of the instrument.

FIG. 15 is a sectional view of the instrument of FIG. 14 along the line 15—15.

DETAILED DESCRIPTION

Figure 16:
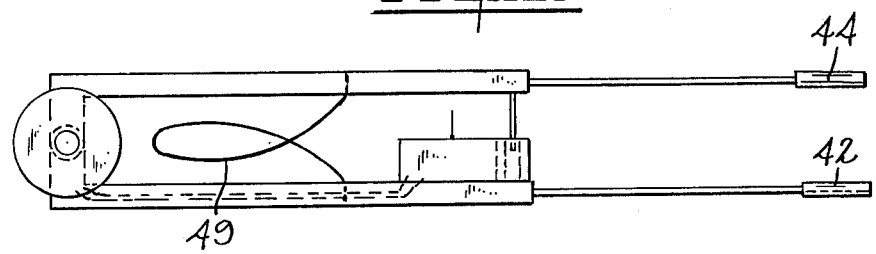
FIG. 16 is a side view of a portion of yet another form of the instrument.
Figure 17:
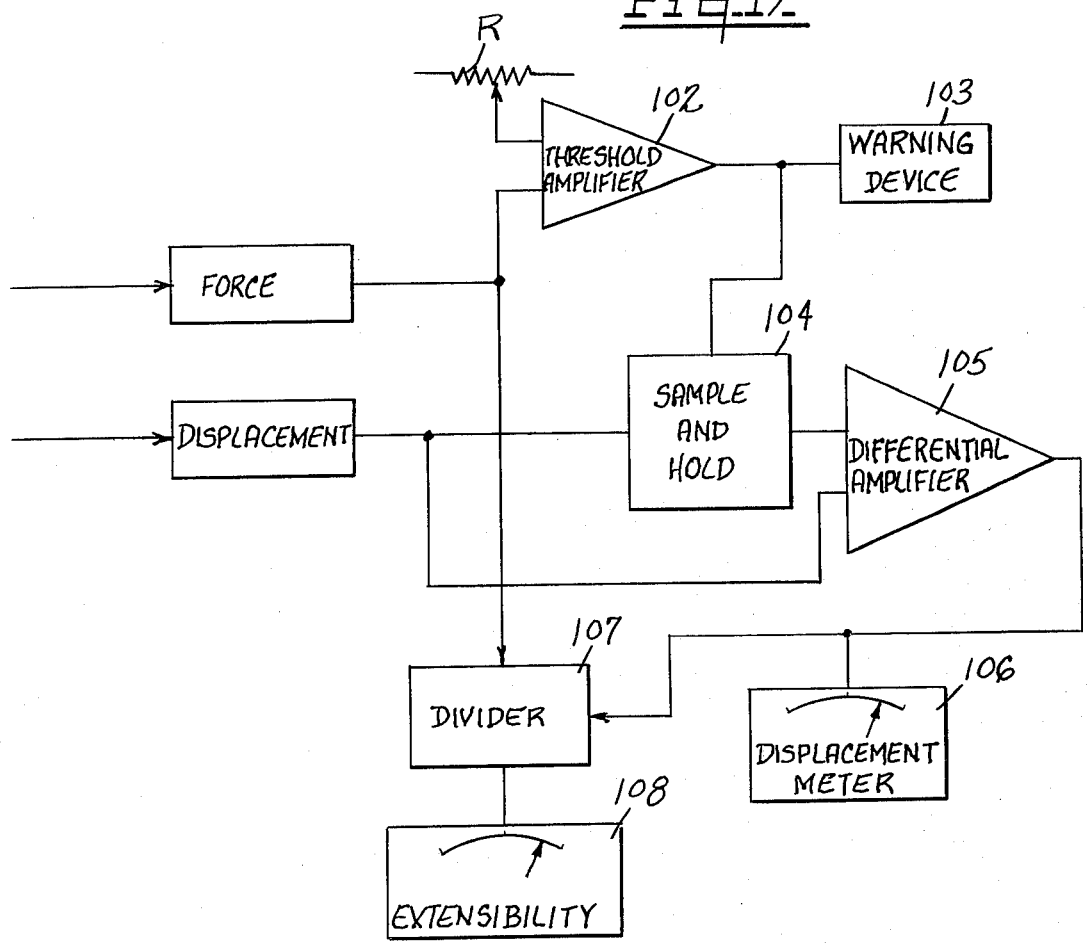
FIG. 17 is a schematic diagram of a circuit employed in the cervical instrument.

With reference to FIG. 1, the cervical instrument shown generally as 10, comprises a probe shown generally as 12 and a process and display assembly shown generally as 14. In FIGS. 1, 3 and 9, probe 12 is constructed in a scissor-like configuration. Probe 12 may be constructed in a variety of other forms such as the tong-like structure illustrated in FIGS. 11, 12, 14 and 16 which are designed for continuous measurement of the cervix.

With further reference to FIGS. 1, 3, 4 and 9, probe 12 comprises an outer arm 20 having a first end 22 and second end 24, and an inner arm 30 having first and second ends 32 and 34, respectively. Arms 20 and 30 are in pivotal engagement at pivot 40. Pivot 40 is intermediate said respective first and second ends so that arms 20 and 30 are in scissor-like arrangement.

Fingers 26 and 36 extend from first ends 22 and 32, respectively. Fingers 26 and 36 are preferably rod-shaped and at each terminus opposite the first ends are further provided with structures which are adapted to engage the lip of the uterine cervix. As such, the structures may assume a variety of forms and configurations. One embodiment of the structures illustrated in FIGS. 1 and 3, comprises an exterior plate 42, in the shape of a concave dish at the end of finger 26, and a convex cylindrical interior plate 44 at the end of finger 36. For purposes of illustration, finger 26 and associated structures such as exterior plate 42 are designated as the probe components which engage tissue exterior to the lip of the cervix and finger 36 and associated structures such as interior plate 44 engage tissue at the interior of the lip. Plates 42 and 44 are preferably dimensioned to complement each other. Finger 26 may further assume an L-shaped configuration as illustrated in FIGS. 1 and 3.

Fingers 26 and 36 may be detachable from the arms 20 and 30 and/or plates 42 and 44 may be detachable from fingers 26 and 36. In this latter regard, it is preferable that all of the foregoing instrument components be manufactured of stainless steel, or similar rigid materials which are relatively difficult to bend or deform and are relatively easy to sterilize.

With reference to FIG. 1, the probe is inserted into the cervix region and positioned so that exterior plate 42 contacts the exterior of the lip of the cervix and interior plate 44 contacts the interior of the lip of the cervix so that a portion of the lip is positioned between the plates. The probe may be positioned at either the anterior or posterior lip. A compressive force applied at second ends 24 and 34 is transferred to effect a corresponding compressive force at plates 42 and 44. The force acts to compress the tissue of the cervix which is positioned between the plates. The compressive force is measured by force measurement device 60. The distance between the contact plates is measured by distance measurement device 50.

A device for measuring the distance between plates 44 and 42 is shown generally as 50 in FIG. 1. Distance measurement device 50 may be of a variety of forms. One form, as further illustrated in FIG. 1, comprises a linear variable differential transformer (LVDT) 52 secured to inner arm 30. Pin 54 extends from LVDT 52 to bear against the top of outer arm 20 under the bias of spring 56.

LVDT 52 is positioned between pivot 40 and second end 34. The scissor-like cooperation between arms 20 and 30 results in the distance between the arms at ends 24 and 34 being proportional to the distance between plates 42 and 44. As the ends 24 and 34 are forced closer together, plates 42 and 44 are forced toward each other. Pin 54 is axially displaced relative to LVDT 52 resulting in an output signal from LVDT 52 which is proportional to the displaced distance of pin 52 and hence is proportional to the relative distance between contact plates 42 and 44.

An alternate embodiment of distance measurement device 50 is illustrated in FIG. 3 in which pin 54 is secured to outer arm 20. This arrangement acts to limit the maximum distance that can be obtained between plates 42 and 44.

The distance measurement device may also be of a form as illustrated in FIGS. 5 and 6. A LVDT 70 is positioned at pivot 40 and in this alternate embodiment, produces an output signal proportional to the relative rotary displacement of a disc 72 which is axially mounted in fixed relation to an axle 74. Axle 74 is in fixed relation to outer arm 20. LVDT 70 is in fixed relation to inner arm 30 except for disc 72 which moves with arm 20. Relative motion between arms 20 and 30 produces a signal output from LVDT 70 indicative of the relative separation of arms 20 and 30, which separation is indicative of the distance between plates 42 and 44.

A still further embodiment of a distance measurement device 50 is illustrated in FIGS. 7 and 8. This latter embodiment is positioned in the same manner as the embodiment of FIGS. 5 and 6. Distance measurement device 50 comprises a housing 80 mounted at pivot 40. A light emitter 82 is positioned within housing 80 to direct light at sensor 84. Sensor 84 is essentially a light meter which produces an output signal indicative of the quantity of light received. A disc 86 is positioned orthogonal to the light path from emitter 82. Disc 86 is axially mounted in fixed relation on axle 87 which is in fixed relation with lower arm 30. Housing 80 is mounted in fixed relation with outer arm 20. Disc 86 is further playing of the extensibility ratio of the uterine cervix throughout the term of labor. Because the uterine cervix is a dynamic entity, equal compressive forces at different times before and during labor may result in unequal tissue displacement measurements. It is apparent that measurements obtained over a period of time during labor may be obtained and the apparent diameter of the cervix can be displayed continuously on a monitor. One operational procedure may involve application of a substantially uniform compressive force to the lip of the cervix during labor, while continuously monitoring the corresponding tissue displacement. The compressibility and thickness of the cervix will decrease until the cervix effaces. The instrument will alert the supervisor by audio or visual means, that the cervix effacement is completed (that is, that the cervical thickness is reduced to a minimal measurement level).

An instrument which is suitable for employing the above operational procedure is illustrated in FIG. 9, where the compressive force may be mechanically fixed (or incrementally varied) over a period of time. The extensibility can be assessed by the compressive force applied to the tissue, and the displacement of the tissue which results from the applied force. If the compressive force is a constant and known quantity, then measurement of the cervical lip diameter as it is determined by the displacement will be sufficient to calculate extensibility.

A number of embodiments of cervical instruments employing a constant pressure between plates 42 and 44 are illustrated in FIGS. 11, 12, 14 and 16. These latter embodiments employ a constant force spring 49. Spring 49 is selected to be capable of producing a constant force regardless of the degree of compression or extension of the spring, over an extension/compression range corresponding to the normal tissue displacement range for a wide sample of patients and/or conditions. Naturally, in all of these latter embodiments, the process and display assembly need only be responsive to the output signal from the distance measurement device because the constant force quantity can be automatically factored into the calculations.

The probe of FIG. 11 comprises upper and lower arms 31 and 33, each having a tongue 46 and 48 extending from the arms. The tongues receive a pin 47 to form a pivot engagement. The distance measurement device may take a variety of forms as previously discussed such as a LVDT as illustrated in FIG. 1, or a light-emitter/sensor as illustrated in FIG. 12 and FIG. 13.

The probe of FIG. 14 illustrates a constant pressure spring positioned proximate the middle of arms 35 and 37, which arms assume a tubulinear type form. The pivot point is at the ends of the arms opposite the contact plates 42 and 44, and the distance measurement device is located at the pivot point as illustrated and previously described with respect to FIG. 5.

It should be noted that the embodiments of FIGS. 11, 12, 14 and 16 are more compact than the other cervical instruments described previously as they are designed to be placed in the vagina. Of particular note is the cervical instrument of FIG. 16 which employs a radio transmitter to relay the distance measurement without wiring to the display assembly.

It may thus be seen that the objects of the invention set forth as well as those made apparent from the foregoing description are efficiently attained. While preferred embodiments of the invention have been set forth for purposes of disclosure, modifications of the disclosed embodiments of the invention as well as other embodiments thereof may occur to those skilled in the art. Accordingly, the appended claims are intended to cover all embodiments of the invention which do not depart from the spirit and scope of the invention.

What I claim is:

1. A method for measuring the modulus curve of extensibility for selected nonexcised tissue of the uterine cervix comprising:
(a) positioning the tissue at the lip of the uterine cervix between two members;
(b) applying an increasing compressive force to the tissue which increases from a minimum force to a maximum force;
(c) measuring the instantaneous force applied and the displacement of tissue resulting from said force over the range of forces applied;
(d) calculating the ratio of the instantaneous force applied to the displacement resulting therefrom;
(e) deriving the modulus curve of extensibility for the uterine tissue from the calculated ratios; and
(f) displaying the modulus curve of extensibility over the range of forces applied.

2. A method for determining changes in the extensibility of selected nonexcised tissue of the uterine cervix, ear or skin comprising:
(a) positioning the tissue between two force transmitting members;
(b) applying a constant compressive force to said tissue through said force transmitting members;
(c) measuring the displacement of the tissue resulting from the application of said force; and
(d) continuously monitoring the changes in the displacement of said tissue over a period of time to determine the changes in the extensibility of said tissue while said constant force is applied.

3. The method of claim 2 wherein the tissue selected is located at the lip of the uterine cervix.

4. The method of claim 2 further comprising calculating the ratio of said constant compressive force and the displacement of said tissue and then visually displaying said ratio.

5. A method for determining the extensibility of selected nonexcised tissue of the uterine cervix, ear or skin comprising:
(a) positioning the tissue between two force transmitting members;
(b) applying a varying compressive force to said tissue over a range of forces;
(c) measuring the force applied and the displacement of said nonexcised tissue resulting from said force over the range of forces applied; and
(d) calculating the modulus curve of extensibility of the tissue over the range of forces applied.

6. The method of claim 5 wherein the tissue selected is located at the lip of the uterine cervix.

7. The method of claim 5 further comprising the step of visually displaying the modulus curve over the range of forces applied.

8. The method of claim 5 wherein changes in the modulus curve of the tissue are continuously monitored as they occur.